United States Patent
Karmali (10) Patent No.: US 8,877,785 B2
(45) Date of Patent: Nov. 4, 2014

(54) METHODS AND COMPOSITIONS FOR ENHANCING SENSITIVITY OF CYTOTOXIC DRUGS WITH TIMELY COMBINATORIAL THERAPY WITH CARBOXYAMIDOTRIAZOLE OROTATE

(75) Inventor: Rashida A. Karmali, Brooklyn, NY (US)

(73) Assignee: Tactical Therapeutics Inc, New York, NY (US)

( * ) Notice: Subject to any disclaimer, the term of this patent is extended or adjusted under 35 U.S.C. 154(b) by 232 days.

(21) Appl. No.: 13/385,449

(22) Filed: Feb. 21, 2012

(65) Prior Publication Data

US 2012/0202760 A1 Aug. 9, 2012

Related U.S. Application Data

(63) Continuation-in-part of application No. 12/807,415, filed on Sep. 3, 2010, now Pat. No. 8,377,973, which is a continuation-in-part of application No. 12/584,448, filed on Sep. 4, 2009, now abandoned.

(51) Int. Cl.

| | | |
|---|---|---|
| *A61K 31/41* | (2006.01) | |
| *A61K 31/395* | (2006.01) | |
| *A61K 31/505* | (2006.01) | |
| *A61P 35/00* | (2006.01) | |
| *C07D 249/04* | (2006.01) | |
| *C07D 487/04* | (2006.01) | |
| *C07D 239/54* | (2006.01) | |

(52) U.S. Cl.
CPC .................................... *C07D 249/04* (2013.01)
USPC ............ 514/359; 548/255; 514/179; 514/183

(58) Field of Classification Search
USPC ................... 548/255; 514/359, 183; 544/179
See application file for complete search history.

(56) References Cited

U.S. PATENT DOCUMENTS

| 7,465,734 | B2   | 12/2008 | Shepard |         |
|-----------|------|---------|---------|---------|
| 7,750,018 | B2 * | 7/2010  | Karmali | 514/274 |
| 8,034,823 | B2 * | 10/2011 | Karmali | 514/274 |
| 8,377,973 | B2 * | 2/2013  | Karmali | 514/359 |
| 8,420,658 | B2 * | 4/2013  | Karmali | 514/267 |

OTHER PUBLICATIONS

Krafte et al., Current Opinion in Pharmacology 2008, 8:50-56.*
Rush et al., Molecular Interventions 2007, vol. 4, issue 7, 192-195.*
Clare et al, Drug Discovery Today 2000, vol. 5, No. 11,506-520.*
Cecil Textbook of Medicine, edited by Bennet, J.C., and Plum F., 20th edition, vol. 1, 1004-101 O, 1996.*
Mass, R. D., Int. J. Radiation Oncology Bio. Phys. vol. 58(3): 932-940, 2004.*
Fabbro et al. Pharmacology & therapeutics 93, 79-98, 2002.*
Kohn Ec et al Cancer Research 1992; 52: 3208-3212.
Ge S et al, Clin Cancer Res 2000; 6:1248-1254.
Alessandro R et al Clin & Exp Metastasis 2002; 19: 265-273.

* cited by examiner

*Primary Examiner* — Venkataraman Balasubramanian
(74) *Attorney, Agent, or Firm* — Rashida A. Kamali, Esq (57) ABSTRACT

This invention relates to enhancing sensitivity of cytotoxic drugs by targeting their interfering mechanisms induced in the tumor microenvironment which lead to drug resistance, using combinatorial therapy with carboxyamidotriazole orotate. Specific doses of cytotoxic drugs are titrated with carboxyamidotriazole orotate to improve the sensitivity and anticancer activity of cytotoxic drugs.

5 Claims, 4 Drawing Sheets

METHODS AND COMPOSITIONS FOR ENHANCING SENSITIVITY OF CYTOTOXIC DRUGS WITH TIMELY COMBINATORIAL THERAPY WITH CARBOXYAMIDOTRIAZOLE OROTATE

CROSS-REFERENCE TO OTHER APPLICATION

This application is a Continuation-in-part of U.S. patent application Ser. No. 12/807,415 filed on Sep. 3, 2010 now U.S. Pat. No. 8,377,973, which is a Continuation-in-part of U.S. patent application Ser. No. 12/584,448 filed on Sep. 4, 2009 now abandoned, which are incorporated herein, with references in their entirety.

1. FIELD OF INVENTION

This invention is related to enhancing the sensitivity of cytotoxic chemotherapeutic and biologic drugs (collectively referred to as "cytotoxic" drugs) in malignant tumors by targeting the initial mechanisms of the cytotoxic drugs in the tumor microenvironment and/or the subsequent development of drug resistance, using combinatorial therapy with carboxyamidotriazole orotate (CTO). More specifically the invention relates to methods and compositions of specific cytotoxic drugs in combination with CTO, a multi-targeted small molecule, to improve the sensitivity of the cytotoxic drugs, to modulate the mechanisms induced by the cytotoxic drugs in the tumor microenvironment and to prevent or reduce the development of drug resistance, thus leading to enhancement of efficacy of the cytotoxic drugs. Such carefully designed combinatorial therapy comprising titrated amounts of the cytotoxic drugs and CTO achieves maximum efficacy without resorting to dose dense strategies which are associated with serious toxicity. Such a combinatorial therapeutic system will improve the quality of life for patients.

2. BACKGROUND TO THE INVENTION

Cytotoxic drugs are now used at some time during the course of the treatment of most cancer patients. Cytotoxic drugs can cure some primary and metastatic cancers and be effective in decreasing tumor volume, treating symptoms and even prolonging life in many types of cancers. The starting dose of the cytotoxic drug in cancer patients is based on preclinical evaluation of the therapeutic dose in different tumor cell lines in vitro and in animal tumor modes in vivo as required by the Guidelines from the Food & Drug Administration for Nonclinical Evaluation for Anticancer Pharmaceuticals (ICH S9). In experimental xenograft tumor models the dose-response curve is usually steep in the linear phase, and a reduction in dose when the tumor is in the linear phase of the dose-response curve, almost always results in a loss in the capacity to cure the tumor effectively before a reduction in the antitumor activity is observed. Although xenograft models may not represent the ideal model for human malignancies, the general principles have been applied to the clinical setting. Such empirical modifications in dose represent a major reason for treatment failure in patients with drug-sensitive tumors who are receiving chemotherapy in either the adjuvant or advanced disease setting.

Another reason for treatment failure in patients with drug-sensitive tumors who are receiving cytotoxic drug is the effect of the cytotoxic drug on the microenvironment of the tumor since the chemotherapy may cause mechanisms that can interfere with its antitumor activity on the tumor itself. The present invention provides a method to include CTO to modulate early and late changes induced by the cytotoxic drug in the microenvironment to minimize the interference with its antitumor activity to improve the sensitivity of the chemotherapy to achieve treatment success. More particularly, CTO is selected as the combinatorial targeted drug to control several of the mechanisms induced in the tumor microenvironment that interfere with the sensitivity and efficacy of the cytotoxic drug.

Since the development of chemotherapy in the 1950s and 1960s that resulted in curative therapeutic strategies for patients with several types of solid tumors and hematologic malignancies the understanding of genetic changes that can result in drug resistance has provided innovative therapeutic strategies; but unfortunately, these studies have not heretofore, considered the early effect of the chemotherapy on the microenvironment of the tumor in the determination of the sensitivity and effective doses required to achieve treatment success. The present invention provides a method for i) evaluating the effect of a cytotoxic drug on the microenvironment of a specific tumor type, ii) identifying the mechanisms that mediate the anticancer activity or that interfere with the anticancer activity, iii) selecting a combinatorial drug, for example CTO, that minimizes or prevents the mechanisms interfering with the anticancer activity, iv) determining the pharmacodynamic interaction between the cytotoxic drugs and the combinatorial chemotherapy with CTO, and v) determining an optimum combination of the cytotoxic drug and CTO to achieve maximum efficacy and least toxicity.

In other words, the present invention provides a method to determine the effective dose of the cytotoxic chemotherapy that is based on enhancing its sensitivity by combining it with carboxyamidotriazole orotate (CTO), an orotate salt of carboxyamidotriazole (CAI). CAI is an inhibitor of receptor-operated calcium channel-mediated calcium influx, and is shown to have antiproliferative and anti-invasive functions in several human cancer cell lines, including human glioblastoma cells (Ge et al, 2000). By interrupting calcium mobilization as a second messenger, CAI can inhibit calcium-sensitive signal transduction pathways, including the release of arachidonic acid and its metabolites; nitric oxide release; the generation of inositol phosphates; and tyrosine phosphorylation (Ge et al, 2000; Kohn et al, 1992). CAI inhibits phosphorylation of cellular proteins STATS and CrkL, and induces apoptosis in imatinib mesylate-resistant chronic myeloid leukemia cells by down-regulating bcr-abl (Alessandro et al, 2008). CTO targets the tumors as well as the microenvironment of the tumor and mechanisms that may induce drug resistance or interfere with the antitumor activity.

The timing and duration of the combination therapy may be determined to be from the start of the cytotoxic drug chemotherapy or at various stages during the therapeutic regimen based on the understanding of the dynamics and extent of the effect of the cytotoxic chemotherapy on the tumor microenvironment. Current principles guiding the selection of chemotherapeutic cytotoxic drugs and of their doses do not consider their impact on the tumor microenvironment. As a result the dose selected to treat a cancer may include an extra amount to overcome early interference in the microenvironment and thus may require reevaluation to achieve optimum treatment success.

Currently, the established dosing regimens for cytotoxic drugs have not factored in this interference in sensitivity of the cytotoxic drugs, hence leading to increase in the dose used. Dose-dense strategies are used to achieve tumor shrinkage but these cause severe toxicities in cancer patients and adversely affect their quality of life. There is a critical need to prevent or reduce this interference in sensitivity instead of using dose dense regimens. The present invention provides a paradigm for the development of new drug therapeutic programs using existing drugs in use or new drugs that design combinations of cytotoxic drugs and CTO where applicable to maximize the sensitivity of the drugs to achieve treatment success rather than taking a does dense approach.

Chemotherapy with cytotoxic drugs is presently used in four main clinical settings: 1) primary induction treatment for advanced disease or for cancers for which there are no other effective treatment approaches, 2) neoadjuvant treatment for patients who present with localized disease for whom local forms of therapy such as surgery and/or radiation are inadequate by themselves, 3) adjuvant treatment to local methods of treatment, including surgery and/or radiation therapy, and 4) direct instillation into sanctuary sites or by site-directed perfusion of specific regions of the body directly affected by the cancer. Physicians" Cancer Chemotherapy Drug Manual, ed, E. Chu, V. T. DeVita, Jr, 2010. The present invention provides a paradigm for the development of new drug therapeutic programs in each of the above four clinical settings to increase the sensitivity of some cytotoxic drugs.

According to the method of the invention, it is 1) necessary to identify whether a tumor is responsive to a specific cytotoxic drug, 2) to identify a profile of molecular targets in the tumor microenvironment that may potentially interfere with its anticancer activity, and 3) to select the most suitable combinatorial regimen of the cytotoxic drug and targeted chemotherapy, for example a cytotoxic drug and CTO. Among the problems currently associated with the use of cytotoxic drugs to treat cancers are the high doses required, toxicity towards normal cells, lack of selectivity and sensitivity, immunosuppression and drug resistance because molecular targets that interfere with the anticancer activity are not controlled.

Drug resistance may also be caused by malignant cells becoming resistant to the drug and a number of cellular mechanisms are probably involved in altering metabolism of the drug, permeability of the cells to the drug or accelerated elimination of the drug, altered specificity of the inhibited enzyme, or amplification of certain genes involved in resistance to chemotherapy or biologic therapy. This is observed after multiple exposures to the drug as described below.

For example, amplification of the gene encoding dihydrofolate reductase is related to resistance to methotrexate, while amplification of the gene encoding thymidylate synthase is related to resistance to treatment with 5-fluoropyridines.

The therapeutic benefit of temozolomide depends on its ability to alkylate/methylate DNA, which most often occurs at the N-7 or O-6 positions of guanine residues. This methylation damages the DNA and triggers the death of tumor cells. However, some tumor cells are able to repair this type of DNA damage, and therefore diminish the therapeutic efficacy of temozolomide by expressing O-6-methyguanine-DNA methytransferase(MSMT) or O-6-alkyguanine—DNA alkyltransferase (AGT or AGAT). In some tumors epigenetic silencing of the MGMT/AGT gene prevents the synthesis of this enzyme, and as a consequence such tumors are sensitive to killing by temozolomide. Conversely, the presence of MGMT protein in brain tumors predicts poor response to temozolomide and these patients receive little benefit. But resistance to temozolomide is related to other factors as well. In GBM patients the tumor responds to temozolomide at first but later, even with increased doses, the tumor becomes refractory after a few courses. This suggests that other interfering factors may be reducing the sensitivity of temozolomide to cancer cells.

Therefore, there is need to understand the mechanism of resistance to temozolomide that may be related to other mechanisms since it is one of the few drugs that crosses the blood brain barrier and used in treatment of malignant gliomas and glioblastoma multiforme, but for the drug resistance that develops after a few courses.

There is some evidence that changes in the tumor microenvironment induced by doxorubicin may impede its delivery to the tumor target and therefore a combinatorial regimen of doxorubicin and CTO may provide a solution to maintain doxorubicin's sensitivity.

In some cases resistance to a drug may be linked to increased production of molecules (e.g., cytokines, calcium channel signaling, molecular signaling) in the tumor microenvironment that interfere with the sensitivity and efficacy of the cytotoxic drugs. Therefore, even the most rationally conceived drug molecule may fail because of mutational changes downstream from its intended target or metabolic features of tumors that never allow the drug to reach its target or that trigger feedback mechanism against the drug molecule.

Thus a rational approach to cancer drug therapy and development is needed that relies on the empirical evidence of tumor shrinkage with cytotoxic drugs, understanding mechanisms of action of the chemotherapy in the tumor microenvironment in real time, defining new lead structures directed to biochemical and molecular targets and causing the cytotoxic drugs to perform optimally. The present invention satisfies this need and provides additional advantages as well. The present invention is distinguishable from the prior art because none of the prior art addresses the issue of preventing and/or reducing the impact of cytotoxic drugs in the tumor microenvironment which interferes with its sensitivity in early stages of therapy before the more permanent biochemical changes lead to the drug resistance in later stages of therapy. The present invention provides a timely combinatorial therapy with CTO that targets the early interference and thus maintains or enhances the sensitivity of the cytotoxic drugs, thus avoiding the need for increase the dose to obtaining optimum efficacy.

The combination of a cytotoxic drug that induces some of the molecular targets controlled by CTO and an appropriate combinatorial dose and regimen of CTO thus provides more effective and less toxic paradigm for new successful cancer treatment programs, a fundamental object of the invention. The pertinent subject matter of the above references is specifically incorporated herein by reference.

3. SUMMARY OF THE INVENTION

The present invention seeks to overcome drawbacks inherent in the prior art by providing a method for identifying cytotoxic drugs currently in use or potential new candidates, and determining an optimum therapeutic dose for each drug when used in combination with an optimum dose of Carboxyamidotriazole orotate (CTO). The combinatorial therapy improves the sensitivity of the cytotoxic drugs to tumor cells, reduces the development of interference and drug resistance in the tumor microenvironment and in the tumor cells and enhances the efficacy of the cytotoxic drugs.

The invention provides methods and compositions for enhancing sensitivity of cytotoxic drugs by targeting the tumor microenvironment to inhibit drug interference and resistance with timely combinatorial therapy with a cytotoxic drug and CTO combination.

The invention provides a paradigm for the development of drug treatment regimens that are based on preclinical and clinical studies to provide i) prior knowledge of the responsiveness of the pathologic category of the tumor to specific chemotherapeutic drugs, ii) an understanding of the cellular, biochemical and molecular targets of the drugs' cytotoxic activity as well as mechanisms of resistance in the tumor microenvironment and in tumor cells of resistance to the drugs, and iii) knowledge of the drugs' pharmacokinetic and pharmacodynamic behavior and patterns of normal organ toxicity.

The invention provides a paradigm that designs a suitable combinatorial regimen of the cytotoxic drugs and a targeted chemotherapy, for example CTO, that targets the cellular, biochemical and molecular targets in the tumor microenvironment of the cytotoxic drugs, such that the combinatorial regimen enhances the sensitivity of the cytotoxic drugs and prevents and/or reduces the development of drug resistance.

The invention provides a shift in the method of developing combinatorial drug regimens by requiring that varying doses of the cytotoxic drug(s) and the targeted chemotherapy (CTO) targeting negative feedback in the tumor microenvironment be tested in preclinical studies in normal rodents as well as in tumor models. Currently, such combinations are based on historical data obtained from studies conducted with individual drugs in preclinical and clinical studies and such prior art overlooks the pharmacodynamic and pharmacokinetic interactions between the drugs, thus putting at risk patients to adverse effects of the drugs. This approach is greatly needed by cancer patients who have to endure severe toxicities when dose dense strategies of cytotoxic drugs are used.

A further embodiment of the invention is development of a combinatorial regiment using a biologic therapeutic agent and a targeted chemotherapeutic agent, for example, CTO to target the negative feedback induced by the biologic in the tumor microenvironment thereby maintain the sensitivity and efficacy of the biologics against the tumor cells.

In view of the foregoing state of the art, the invention provides has combinatorial designs of drug combinations in preclinical studies that provide reliable information on toxicity of the varying combinations of combination regimen in normal versus tumor bearing models. In other words, the invention will reduce the risk of development of drug regimens first in patient and avoid risk to the patients.

It is the object of the invention to provide methods to design optimum combinatorial compositions of one or more cytotoxic drugs and one or more targeted chemotherapeutic drug, for example, CTO to increase the sensitivity of the cytotoxic drugs, to enhance the treatment effects and to reduce toxicity in the long term by using optimum and generally lower doses. In other words, the invention provides a paradigm of dose dilution by timely combinatorial strategies. There is great need for such strategy to improve the quality of life for patients by diluting the dose of chemotherapy.

Such an approach described above has resulted in unexpected important findings with several cytotoxic drugs when combined with CTO on the sensitivity and efficacy of the cytotoxic drugs. More importantly, it was found that that the combination of lower doses of previously configured therapeutic doses of cytotoxic drugs with CTO, actually results in higher efficacy. This dose-diluting combinatorial strategy fulfills the need for reducing drug resistance, increasing sensitivity, increasing efficacy and reducing the toxicity compared with currently used dose dense strategies. This invention provides an important and novel approach not only to obtain better efficacy using lower doses of previously set therapeutic doses but also the related reduction in toxicity.

5. DETAILED DESCRIPTION OF THE INVENTION

The invention is achieved by evaluating the cellular, biochemical and molecular targets of cytotoxic drugs in the tumor microenvironment and by exploiting some of the key genomic and phenotypic changes linked to resistance to cytotoxic drugs by cancer cells. The invention provides a paradigm for i) selecting a cytotoxic drug for a specific cancer, ii) evaluating the effect of this agent on cellular, biochemical and molecular targets in the tumor microenvironment in vitro or in vivo, iii) selecting a combinatorial chemotherapy that inhibits the targets induced in the tumor microenvironment to inhibit or prevent resistance by the targets, to titrate varying combinations of the cytotoxic drugs and the targeted chemotherapy, for example CTO, in preclinical toxicology studies and efficacy studies in non-tumored mice, and iv) to establish the human starting dose thereof.

This paradigm for development of therapeutic regimens aims for an optimum combination of the two or more drugs selected to achieve the maximum efficacy and least drug related toxicity. Such an approach to developing cancer therapeutic programs is long overdue and there is great need for it to ensure successful treatments and safety of patients by preventing overdosing with cytotoxic cancer drugs.

Chemotherapy Dosing Schedule Influences Drug Resistance Development in Several Cancers Drug resistance is the leading cause of chemotherapy failure in the treatment of cancer and is responsible for the death of a great majority of patients with metastatic late-stage cancer. Patients initially respond well to chemotherapy. However, cancer cells have significant plasticity and multiple cycles of chemotherapy have been shown to select tumor cells that are inherently resistant or that have developed resistance over the course of treatment and eventually, the disease becomes incurable.

Chemotherapy Interference and Resistance in Tumor Microenvironment

Drug resistance can result from both tumor microenvironmental and molecular factors in cancer cells. Issues such as hypoxic regions, irregular blood flow and supply, the extracellular matrix, high density of cells within the tumor, high intersticial fluid pressure can create pharmacologic and physical barriers through which chemotherapeutic drugs cannot diffuse and reach the tumor. Alternatively drug delivery to tumor cells can be hindered by upregulation of cell membrane drug efflux transporters. The product of the MDR 1 gene, P-glycoprotein (P-gp) is a key molecule leading to cancer multidrug resistance. Mounting evidence suggests that bone-marrow-derived cells (BMDC) contribute to tumor growth, angiogenesis and metastasis. Importantly, in acute reactions to cytotoxic chemotherapy, several types of BMDCs are rapidly mobilized in tumors. These BMDC and plasma from chemotherapy treated mice promote metastatic properties in tumor cells by inducing matrix metalloproteinase-9 (MMP9) and epithelial-to-mesencymal transition. In mice in which Lewis lung carcinoma cells were injected intravenously, treatment with paclitaxel, a cytotoxic agent, accelerated metastases in a manner that could be blocked by an MMP9 inhibitor. Therefore, inhibition of MMP9 by using a combinatorial regimen of paclitaxel and an MMP9 inhibitor could inhibit the metastases.

Similarly, some angiogenic therapies have been shown to paradoxically enhance vascular function. Targeting VEGF receptors using antibodies results in temporary improvement in vascular function, termed "vascular normalization" and is associated with a reduction in tumor hypoxia and increased radiation sensitivity. However, the transient nature of this response makes it difficult to translate into clinical practice. Over expression of VEGF is linked to oncogenic signaling and VEGF induction can be triggered by RAS signaling through phosphoinositide-3 kinase (PI3K) pathway. Signal transduction arising from PI3 kinase in particular plays a major role in cancer cell signaling. Therefore, combinatorial therapy with anti-VEGF, for example, CTO, may prevent the vascular improvement and improve the anti-angiogenic therapy. Similarly, PI3 kinase inhibitor, such as CTO, given with a chemotherapeutic cytotoxic may improve the delivery of the cytotoxic to the tumor and improve efficacy. CTO inhibits PI3 kinase activity by inhibiting conversion of PI2 to PI3. In addition, CTO is an inhibitor of calcium signaling and channeling which is important in the vertical targeting of PI3 kinase and in cancer cell proliferation. CTO is an inhibitor of VEGF which is required by malignant melanoma cells for growth. However, targeted therapy with VEGF blockers such as bevacizumab or Aflibercept® as monotherapy has failed to reduce the tumor burden and their combinations with cytotoxic drugs have failed in melanoma treatment.

Chemotherapy Interference and Resistance Due to Molecular Factors

Chemotherapy resistance occurs when cancers that have been responding to a therapy suddenly begin to grow. In other words, the cancer cells are resisting the effects of the chemotherapy. The drugs will need to be changed or the dose increased. There are several possible reasons for chemotherapy resistance at the molecular level. Some of the cancer cells that are not killed by the chemotherapy mutate and become resistant to the drug. Once they multiply they may be more resistant to the chemotherapy. Another reason is gene amplification. A cancer cell may produce hundreds of copies of a particular gene, which triggers an overproduction of proteins that render the chemotherapeutic drug ineffective. Yet another reason is that cancer cells may pump out of the cell the drug using p-glycoprotein or the cancer cell stops taking in drugs because the protein that transports the drug across the cell wall stops working. Another reason is that cancer cells develop mechanisms to inactivate the drug or to repair the DNA breaks caused by the drug. In other words, when treating cancer the best weapon is the smallest possible interference in the drug sensitivity and chemotherapy resistance.

Melanoma is a highly vascular tumor where VEGF is linked to pathogenesis and poor prognosis in melanoma patients. The molecular heterogeneity in melanoma makes it difficult to maintain the response of the BRAF inhibitors and it is suggested that PI3 kinase may limit the degree to which BRAF mutant melanoma remain sensitive to BRAF inhibitors.

Some drugs are toxic by themselves, but their toxicity may be potentiated when they are used in combination with other agents, the combination may be more toxic than the sum of the toxicities of the individual components. The idea that tissue damage associated with chemotherapy can activate a paracrine prosurvival secretory program suggests that inhibition of signaling pathways activated by IL-6 might potentiate the therapeutic efficacy of conventional chemotherapeutic cytotoxics.

Examples of Chemotherapeutic Cytotoxic Drugs Demonstrating Drug Resistance

Temozolomide is an oral alkylating agent which has been used for the treatment of Grade IV astrocytoma, an aggressive brain tumor also known as glioblastoma multiforme. It is also used for treatment of melanoma a form of skin cancer, Grade III Anaplastic Astrocytoma and oligodendroglioma and malignant gliomas in adults and children. Laboratory studies and clinical trials are investigating whether it might be possible to further increase the anticancer potency of temozolomide by combining it with other agents.

The invention provides methods and compositions that further improve the antitumor activity of temozolomide. Specifically the invention provides a combinatorial therapeutic regimen of temozolomide and CTO to enhance sensitivity and antitumor activity.

More particularly, the combinatorial regimen is designed by first titrating the two drugs in non-tumored mice to determine the range of tolerated doses of the combination.

The next step in the paradigm is to use the tolerated doses in tumor-mice and to evaluate the most effective combination to achieve the treatment effect.

The invention describes highly unexpected and novel results showing that the best combinatorial therapeutic effect is observed when lower doses of the cytotoxic drug and lower doses of CTO are used. Contrary to the published literature and actual clinical practice, the present invention describes methods and compositions based on dose dilution to achieve maximum treatment effect.

It is an objective of the present invention to reduce the interference caused by the cytotoxic drugs in the tumor microenvironment, by using them in combinatorial regimens with CTO, a small molecule that has multiple functional targets, some of which involved in loss of sensitivity of cytotoxic drugs and in the development of drug resistance, as exemplified in detail below.

6. EXAMPLES

Example 1

Titration of Combinatorial Therapeutics in Normal Mice

The purpose of the first experiment was to evaluate the tolerance of female athymic NCr-nu/nu mice to the combination treatment of 5-amino-1-(4-(4-chlorobenzoyl)-3,5-dichlorobenzyl)-1,2,3-triazole-4-carboxyamide orotate (CTO) and a cytotoxic chemotherapeutic agent selected from the group consisting of temozolomide, 5-FU, methotrexate, doxorubicin and daunorubicin.

Polyethylene glycol (PEG 400, MW 400) was purchased from Aldrich Chemistry. Deionized water was purchased from LabChem, Inc. Klucel (hydroxypropyl cellulose) was purchased from Aldrich. Saline (physiological saline solution, for animal use only) was purchased from Nova-Teck, Inc. Tween 80 (T80, polysorbate 80) was purchased from Fisher Scientific. CTO (MW 580.76) was stored at room temperature protected from light upon receipt. CTO was formulated once a week (on Days 1 and 8) at a concentration of 51.3 mg/mL in 40% PEG 400 in deionized water. Temozolomide® (temozolomide, Schering Co., 20 mg/capsule) was prepared on each day treatment by adding several drops of T80 to the powder, and then adding 0.3% Klucel in saline to yield a concentration of 4.5 mg/mL.

The study consisted of four groups of five mice per group for a total of 25 mice on Day 1. Animals in Group 1 were treated with CTO at a dose of 513 mg/kg/dose once a day for fourteen consecutive days (Q1Dx14, Days 1-14) in combination with temozolomide which was administered at a dose of 90 mg/kg/dose once every four days for a total of three treatments (Q4Dx3, Days 1, 5, and 9). Animals in Group 2 were treated with CTO at a dose of 342 mg/kg/dose on a Q1Dx14 schedule, in combination with temozolomide which was administered at a dose of 90 mg/kg/dose on a Q4Dx3 schedule. Animals in Group 3 were treated with CTO at a dose of 513 mg/kg/dose on a Q1Dx14 schedule, in combination with temozolomide which was administered at a dose of 60 mg/kg/dose on a Q4Dx3 schedule. Animals in Group 4 were treated with CTO at a dose of 342 mg/kg/dose on a Q1Dx14 schedule, in combination with temozolomide which was administered at a dose of 60 mg/kg/dose on a Q4Dx3 schedule. Individual body weights are presented in Table 1.

TABLE 1

Mean Body Weight (g)

| Day | 1 | 4 | 8 | 11 | 15 | 18 | 22 |
| --- | --- | --- | --- | --- | --- | --- | --- |
| Group 1 | 21.9 | 20.6 | 20.8 | 21.2 | 22.6 | 23.6 | 24.3 |
| Group 2 | 22.4 | 22.0 | 21.4 | 21.9 | 23.4 | 24.1 | 25.1 |
| Group 3 | 23.7 | 22.3 | 22.8 | 23.0 | 25.2 | 26.3 | 26.9 |
| Group 4 | 24.4 | 23.0 | 23.7 | 24.4 | 25.3 | 25.9 | 26.5 |

RESULTS—Administration of CTO at a dose of 513 mg/kg/dose in combination with temozolomide at a dose of 90 or 60 mg/kg/dose (Groups 1 and 3, respectively) was associated with a maximum mean body weight loss of 6% (1.3-1.4 g), observed on Day 4. Administration of CTO at a dose of 342 mg/kg/dose in combination with temozolomide at a dose of 90 mg/kg/dose (Group 2) was associated with a maximum mean body weight loss of 4% (1.0 g), observed on Day 8. Administration of CTO at a dose of 342 mg/kg/dose in combination with temozolomide at a dose of 60 mg/kg/dose (Group 4) was associated with a maximum mean body weight loss of 6% (1.4 g), observed on Day 4. Animals in all four groups gained weight after the end of the treatment. Thus, the maximum tolerated dose (MTD) was above 513 mg/kg/dose for CTO and 90 mg/kg/dose for temozolomide in this experiment. MTD is defined ad the dose which does not result in death or produces no more than 20% mean body weight loss.

Example 2

Cominatorial Therapy with Temozolomide and CTO in Xenograft Model of Human LOX IMVI Melanoma in Mice The purpose of the experiment TTI-6A was to evaluate the antitumor activity of CTO when administered in combination with temozolomide against subcutaneously (SC)-implanted human LOX IMVI melanoma xenografts in female, athymic NCr-nu/nu mice. Female six-week-old athymic NCr-nu/nu mice were purchased from Charles River Laboratories (Wilmington, Mass.). Human LOX IMVI melanoma cells were maintained as an ascites passage. Each mouse was implanted SC near the right flank with one million ($1 \times 10^6$) of the LOX IMVI human melanoma cell from an in vivo passage using a 23 g needle. The day of tumor fragment implantation was designated as Day 0. Individual tumors of 90 animals grew to 126-198 mg in weight (126-198 mm³ in size) on Day 6 after tumor implantation (Jul. 20, 2011), the day of treatment initiation. Those animals selected with tumors in the proper size range were assigned to nine treatment groups so that the mean tumor weights in all groups on Day 6 were as close to each other as possible (mean tumor weights being 165 or 166 mg, median tumor weights ranging from 162 to 176 mg).

CTO was administered to mice by exact individual animal's body weight on each day of treatment, with the injection volume being 0.1 mL/10 g body weight. temozolomide dosing formulations were administered to mice within 30 minutes of formulation by exact individual body weight on each day of treatment, with the injection volume being 0.2 mL/10 g body weight.

The study consisted of nine groups of ten mice per group. Animals in Group 1 were treated with the CTO vehicle (40% PEG 400 in deionized water) on a Q1Dx14 schedule (Days 6-19) in combination with the temozolomide vehicle (0.3% Klucel in saline), which was administered on a Q4Dx3 schedule (Days 6, 10, and 14). Animals in Groups 2 and 3 were treated with CTO at doses of 513 and 342 mg/kg/dose, respectively, on a Q1Dx14 schedule. Animals in Groups 4 and 5 were treated with temozolomide at, doses of 90 and 60 mg/kg/dose, respectively, on a Q4Dx3 schedule. Animals in Groups 6 and 7 were treated with CTO on a Q1Dx14 schedule at doses of 513 and 342 mg/kg/dose, respectively, in combination with temozolomide which was administered at a dose of 90 mg/kg/dose on a Q4Dx3 schedule. Animals in Groups 8 and 9 were treated with CTO on a Q1Dx14 schedule at doses of 513 and 342 mg/kg/dose, respectively, in combination with temozolomide which was administered at a dose of 60 mg/kg/dose on a Q4Dx3 schedule.

The SC tumors were measured and the animals were weighed two times a week. Tumor volume was determined by the formula for an ellipsoid sphere: $L \times W^2/2 = mm^3$, where L and W refer to the larger and smaller perpendicular dimensions collected at each measurement. The experiment was terminated on Day 35.

Figure 1:
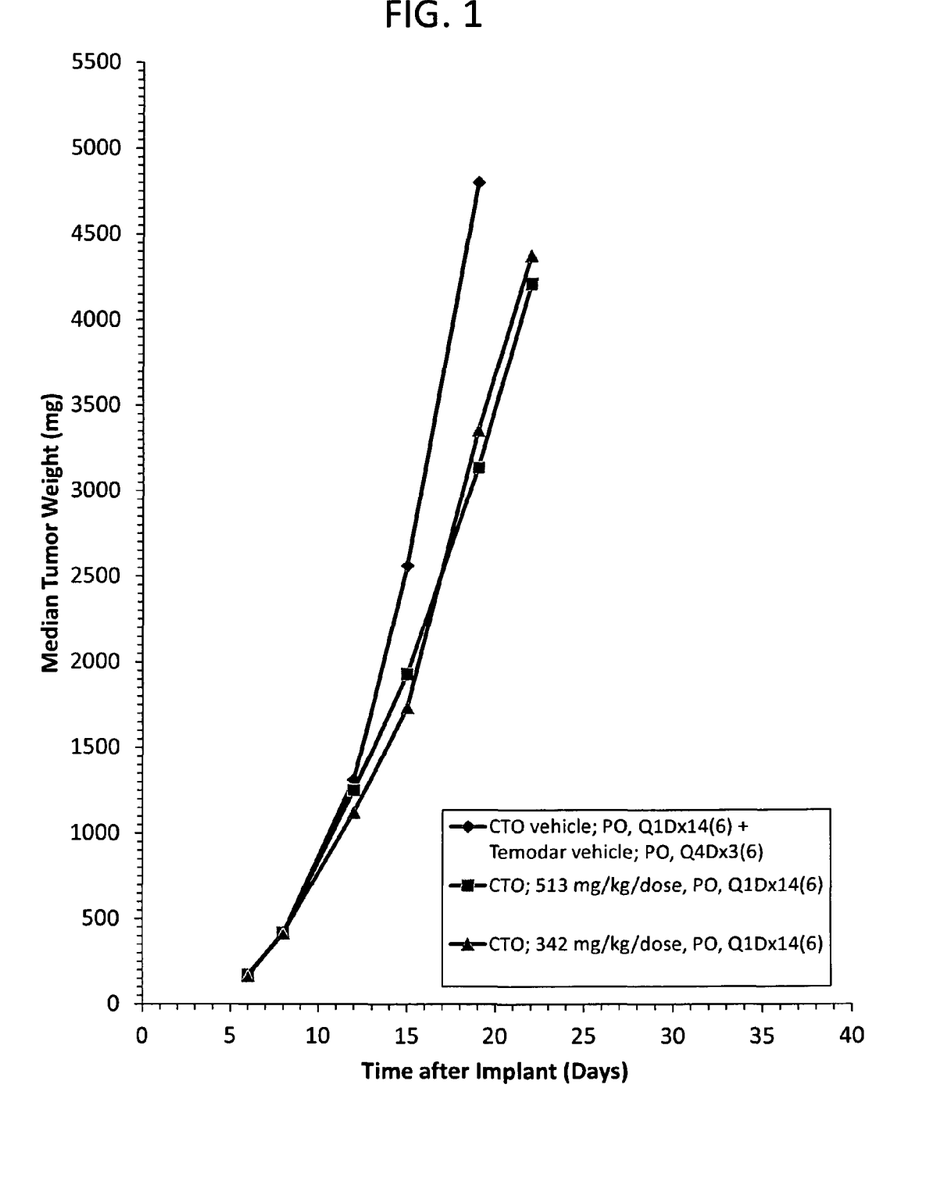
FIG. 1 illustrates the response of SC Implanted LOX IMVI Human Melanoma to Treatment with different doses of CTO.

Parameters Evaluated—Number of nonspecific deaths, number of complete tumor regressions, number of tumor-free survivors on Day 35, and the median time for the tumors to reach four tumor mass doublings were determined. Comparison of the median tumor weight in the treatment groups to the median tumor weight in the control group (T/Cx100%) on Day 19 (the last day of treatment with CTO and the last day of data collection when mice in the control group were still alive) was used for an additional evaluation of the antitumor efficacy of the combination treatments. Results are summarized in FIGS. 1-4. Oral administration of CTO at doses of 513 and 342 mg/kg/dose (Groups 2 and 3, respectively) was associated with maximum mean body weight losses of 4% (0.9 g) and 2% (0.6 g), respectively, observed on Day 8. Growth of the tumors in the groups treated with CTO at both doses was found to be statistically different from the growth of the tumors in the control group, when individual animal's times to reach four tumor mass doublings were compared (Group 1 vs. Group 2: P<0.001; Group 1 vs. Group 3: P=0.004). The T/C values on Day 19 were 65% and 70%, respectively. Tumor weights on Day 19 in both CTO-treated groups were statistically different from the tumor weights in the vehicles-treated control group (Group 1 vs. Group 2: P<0.001; Group 1 vs. Group 3: P=0.010). The observed antitumor activity was not dose-dependent when individual animal's times to reach four tumor mass doublings were compared (Group 2 vs. Group 3: P=0.556) and when individual animal's tumor weights on Day 19 were compared (Group 2 vs. Group 3: P=0.204). FIG. 1.

Figure 2:
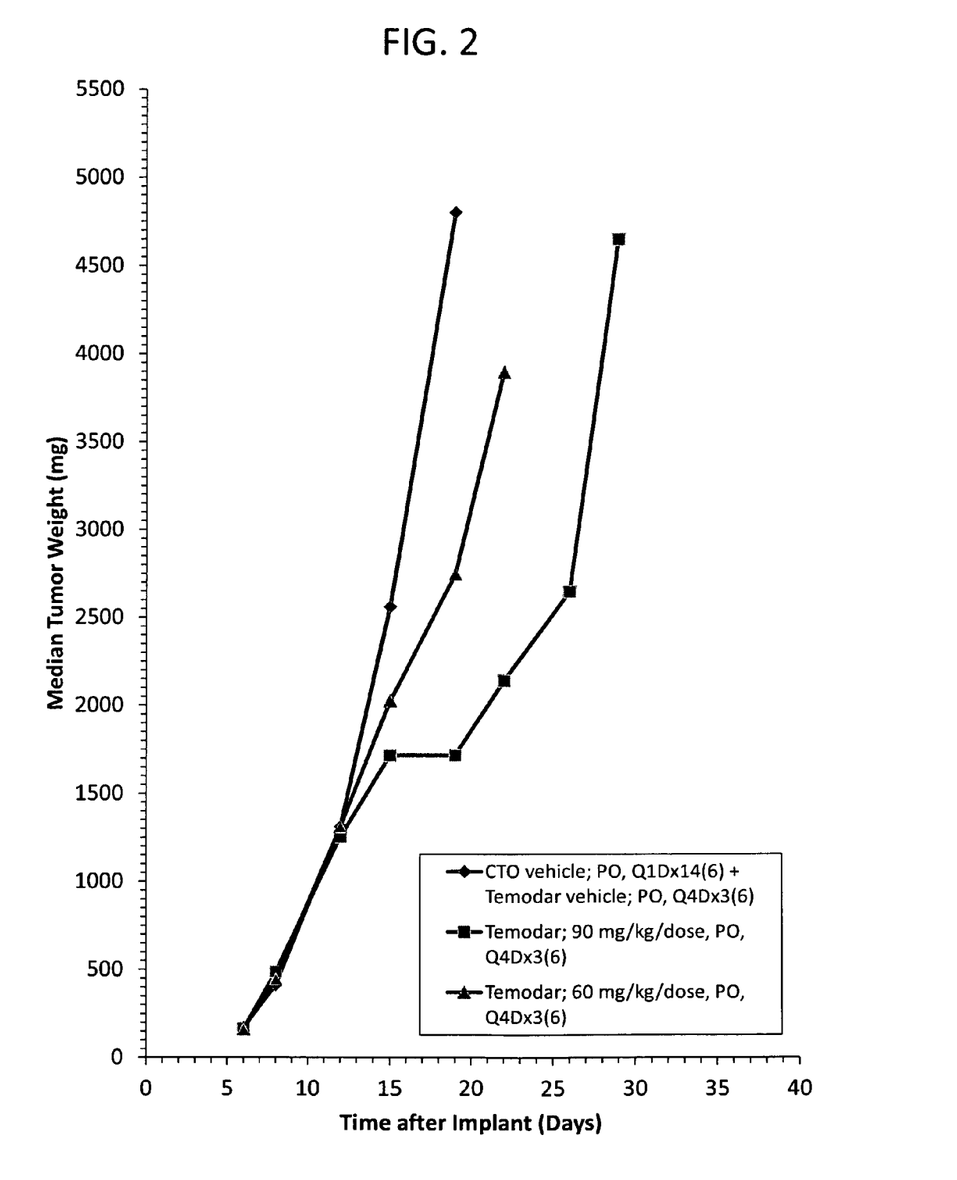
FIG. 2 illustrates the response of SC Implanted LOX IMVI Human Melanoma to Treatment with different doses of temozolomide

Oral administration of temozolomide at doses of 90 and 60 mg/kg/dose (Groups 4 and 5, respectively) was associated with maximum mean body weight loss of 7% (1.6-1.8 g) in both groups. The median tumor reached four tumor mass doublings in 17.2 and 12.3 days, producing a delay in the growth of the median tumor of 8.5 and 3.6 days, respectively. Growth of the tumors in both temozolomide-treated groups was found to be statistically different from the growth of the tumors in the control group, when individual animal's times to reach four tumor mass doublings were compared (P<0.001 for both groups). The T/C values on Day 19 were 36% and 57%, respectively. Tumor weights on Day 19 in both groups treated with temozolomide were statistically different from the tumor weights in the vehicles-treated control group (P<0.001 for both groups). The observed antitumor activity was dose-dependent when individual animal's times to reach four tumor mass doublings were compared (Group 4 vs. Group 5: P<0.001) and when individual animal's tumor weights on Day 19 were compared (Group 4 vs. Group 5: P=0.004). FIG. 2.

Figure 3:
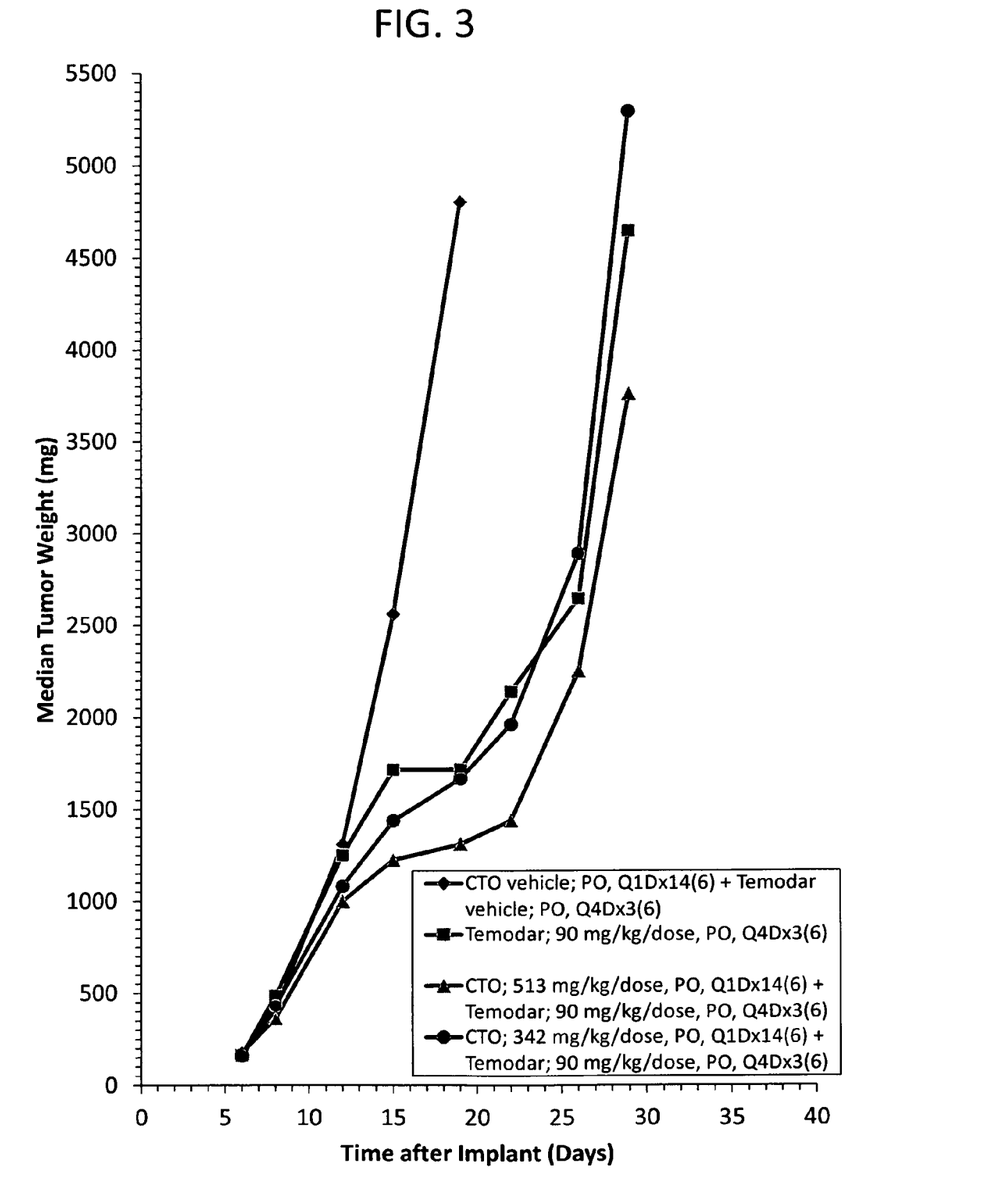
FIG. 3 illustrates the response of SC Implanted LOX IMVI Human Melanoma to Treatment with different doses of CTO with the High Dose of Temozolomide (90 mg/kg/dose)

Administration of CTO at a dose of 513 mg/kg/dose in combination with temozolomide at a dose of 90 mg/kg/dose (Group 6) was associated with a maximum mean body weight loss of 16% (3.7 g), observed on Day 22. The median tumor reached four tumor mass doublings in 20.2 days, producing a delay in the growth of the median tumor of 11.5 days. Growth of the tumors in this combination treatment group was found to be statistically different from the growth of the tumors in the control group, when individual animal's times to reach four tumor mass doublings were compared (Group 1 vs. Group 6: P<0.001); however, tumor growth was not different from the growth of the tumors in the group treated with temozolomide at a dose of 90 mg/kg/dose alone (Group 4 vs. Group 6: P=0.383). The T/C value on Day 19 was 27%. Tumor weights on Day 19 in this combination group were statistically different from the tumor weights in the vehicles-treated control group (Group 1 vs. Group 6: P<0.001) and from the tumor weights in the group treated with temozolomide at a dose of 90 mg/kg/dose alone (Group 4 vs. Group 6: P=0.021).

Administration of CTO at a dose of 342 mg/kg/dose in combination with temozolomide at a dose of 90 mg/kg/dose (Group 7) was associated with a maximum mean body weight loss of 15% (3.5 g), observed on Days 19 and 22. Three animals in the group died (with deaths occurring on Days 19, 25, and 28). The median tumor reached four tumor mass doublings in 16.9 days, producing a delay in the growth of the median tumor of 8.2 days. Growth of the tumors in this combination treatment group was found to be statistically different from the growth of the tumors in the control group, when individual animal's times to reach four tumor mass doublings were compared (Group 1 vs. Group 7: P<0.001); however, tumor growth was not different from the growth of the tumors in the group treated with temozolomide at a dose of 90 mg/kg/dose alone (Group 4 vs. Group 7: P=0.890). The T/C value on Day 19 was 35%. Tumor weights on Day 19 in this combination group were statistically different from the tumor weights in the vehicles-treated control group (Group 1 vs. Group 7: P<0.001); however, tumor weights were not different from the tumor weights in the group treated with temozolomide at a dose of 90 mg/kg/dose alone (Group 4 vs. Group 7: P=0.211). FIG. 3.

Figure 4:
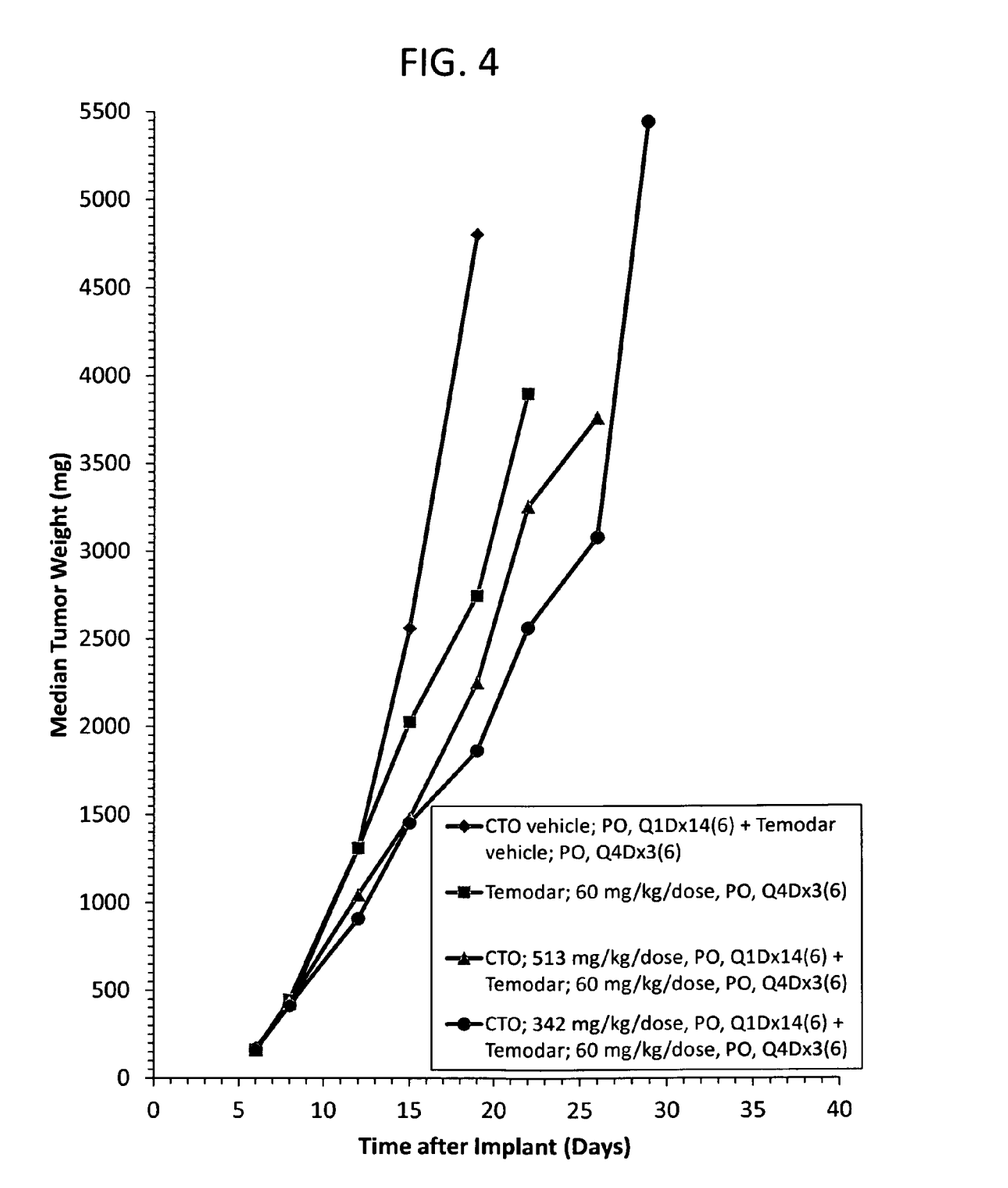
FIG. 4 illustrates the response of SC Implanted LOX IMVI Human Melanoma to Treatment with different doses of CTO with the Low Dose of Temozolomide (60 mg/kg/dose)

Administration of CTO at a dose of 513 mg/kg/dose in combination with temozolomide at a dose of 60 mg/kg/dose (Group 8) was associated with a maximum mean body weight loss of 8% (2.0 g), observed on Day 22. The median tumor reached four tumor mass doublings in 15.5 days, producing a delay in the growth of the median tumor of 6.8 days. Growth of the tumors in this combination treatment group was found to be statistically different from the growth of the tumors in the control group, when individual animal's times to reach four tumor mass doublings were compared (Group 1 vs. Group 8: P<0.001) and from the growth of the tumors in the group treated with temozolomide at a dose of 60 mg/kg/dose alone (Group 5 vs. Group 8: P=0.001). The T/C value on Day 19 was 47%. Tumor weights on Day 19 in this combination group were statistically different from the tumor weights in the vehicles-treated control group (Group 1 vs. Group 8: P<0.001) and from the tumor weights in the group treated with temozolomide at a dose of 60 mg/kg/dose alone (Group 5 vs. Group 8: P=0.017). The antitumor activity of the combination treatment was additive compared to the antitumor activity produced by the administration of each compound alone: a median tumor growth delay in Group 2 (CTO at a dose of 513 mg/kg/dose)=3.1 days, a median tumor growth delay in Group 5 (temozolomide at a dose of 60 mg/kg/dose)=3.6 day compared to a median tumor growth delay in Group 8 (CTO at a dose of 513 mg/kg/dose plus temozolomide at a dose of 60 mg/kg/dose)=6.8 days.

Administration of CTO at a dose of 342 mg/kg/dose in combination with temozolomide at a dose of 60 mg/kg/dose (Group 9) was associated with a maximum mean body weight loss of 10% (2.2-2.3 g), observed on Days 15 and 19. One animal died on Day 19. The median tumor reached four tumor mass doublings in 19.4 days, producing a delay in the growth of the median tumor of 10.7 days. Growth of the tumors in this combination treatment group was found to be statistically different from the growth of the tumors in the control group, when individual animal's times to reach four tumor mass doublings were compared (Group 1 vs. Group 9: P<0.001) and from the growth of the tumors in the group treated with temozolomide at a dose of 60 mg/kg/dose alone (Group 5 vs. Group 9: P<0.001). The T/C value on Day 19 was 39%. Tumor weights on Day 19 in this combination group were statistically different from the tumor weights in the vehicles-treated control group (Group 1 vs. Group 9: P<0.001) and from the tumor weights in the group treated with temozolomide at a dose of 60 mg/kg/dose alone (Group 5 vs. Group 9: P=0.001). The antitumor activity of the combination treatment was more than additive compared to the antitumor activity produced by administration of each compound alone: a median tumor growth delay in Group 3 (CTO at a dose of 342 mg/kg/dose)=1.6 days, a median tumor growth delay in Group 5 (temozolomide at a dose of 60 mg/kg/dose)=3.6 day compared to a median tumor growth delay in Group 9 (CTO at a dose of 342 mg/kg/dose plus temozolomide at a dose of 60 mg/kg/dose)=10.7 days. FIG. 4.

Therefore, oral administration of CTO at doses of 513 or 342 mg/kg/dose for fourteen consecutive days resulted in a measurable inhibition of the growth of the human LOX IMVI melanoma xenografts when implanted SC in female athymic NCr-nu/nu mice. The observed antitumor activity of CTO was not dose-dependent. Oral administration of temozolomide at doses of 90 and 60 mg/kg/dose once every four days for a total of three treatments resulted in a measurable, dose-dependent inhibition of the growth of the human LOX IMVI melanoma xenografts. While the combination treatment of CTO at both doses tested with temozolomide at a dose of 90 mg/kg/dose did not result in an increased antitumor activity compared to the antitumor activity produced by the administration of temozolomide alone at a dose of 90 mg/kg/dose, the combination treatment of CTO at both doses tested with temozolomide at a dose of 60 mg/kg/dose resulted in an increased antitumor activity compared to the antitumor activity produced by the administration of temozolomide alone at a dose of 60 mg/kg/dose. While the antitumor activity of the combination treatment of CTO at a dose of 513 mg/kg/dose plus temozolomide at a dose of 60 mg/kg/dose was additive, the antitumor activity of the combination treatment of CTO at a dose of 342 mg/kg/dose plus temozolomide at a dose of 60 mg/kg/dose was more than additive. These results demonstrate that the dose dilution strategy of using lower doses of temozolomide produced the maximum antitumor activity. This is contrary to the established practice of dose dense strategies currently used in treating cancer patients and promises to make a huge impact on achieving maximum treatment effects and lower toxicities through the "dose dilution" strategy.

The present invention is not to be limited in scope by the embodiment disclosed in the example which is intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

Those skilled in the art will recognize, or be able to ascertain using no more than routine experimentation, any equivalents to the specific embodiments of the invention described herein. Such equivalents are intended to be encompassed by the claims.

What is claimed is:

1. A method of increasing the anticancer activity towards a chemotherapeutic drug used to treat a tumor, wherein the tumor is melanoma, said method comprising:
    administering a sufficient amount of the chemotherapeutic drug to a subject in need thereof, wherein the chemotherapeutic drug consists of temozolomide,
    identifying the mechanisms induced in the tumor microenvironment that may interfere with the anticancer activity,
    administering a sufficient amount of a drug consisting of carboxyamidotriazole orotate to induce anticancer activity and to target the mechanisms identified that interfere with the anticancer activity in the tumor microenvironment,
    measuring the pharmacodynamic interaction between temozolomide and carboxyamidotriazole orotate to determine the time of administration and an optimum combinatorial dose of each drug that achieves therapeutic levels, and
    administering the pre-determined optimum combinatorial dose to achieve maximum anticancer activity, least interference in the microenvironment or least toxicity to non-tumored cells.

2. A method of increasing the sensitivity towards the chemotherapeutic drug, temozolomide, said method comprising:
    administering different doses of temozolomide to normal animals to determine a maximum tolerated dose and blood levels of temozolomide in normal animals,
    identifying the mechanisms induced by temozolomide that interfere with the chemotherapeutic activity,
    administering different doses of carboxyamidotriazole orotate to normal animals to determine the maximum tolerated dose and blood levels of carboxyamidotriazole orotate in the normal animals,
    selecting 2 testing dose levels of temozolomide below the maximum tolerated dose determined, the two testing doses referred to as high temozolomide dose and low temozolomide dose respectively,
    selecting 2 testing dose levels of carboxyamidotriazole orotate below the maximum tolerated dose determined, the two testing doses referred to as high carboxyamidotriazole orotate dose and low carboxyamidotriazole orotate dose respectively,
    designing 4 combinatorial doses a) to d) by combining the 2 testing dose levels of temozolomide with the 2 testing dose levels of carboxyamidotriazole to produce a) low temozolomide+low carboxyamidotriazole, b) low temozolomide+high carboxyamidotriazole, c) high temozolomide+low carboxyamidotriazole and d) high temozolomide+high carboxyamidotriazole orotate,
    administering each of the 4 combinatorial doses a) to d) to normal animals,
    measuring the pharmacodynamic interaction between the temozolomide and carboxyamidotriazole orotate in each of combinatorial dose a) to d) administered by measuring blood levels and body weights, and
    determining an optimum combinatorial dose that exhibits least body weight loss and achieves therapeutic levels in the blood.

3. The method according to claim 2 for selecting the pre-determined optimum combinatorial dose in normal animals, further comprising
    testing the pre-determined optimum combinatorial dose in animals implanted with tumors to achieve maximum antitumor activity and least toxicity.

4. A pharmaceutical composition of a pre-determined optimum dose of the combinatorial dose of temozolomide and carboxyamidotriazole orotate that achieves the maximum antitumor activity and demonstrates least toxicity.

5. The pharmaceutical composition according to claim 4 wherein the optimum combinatorial dose of temozolomide and carboxyamidotriazole is estimated by the method comprising:
    (1) determining the maximum tolerated dose of each in normal animals,
    (2) selecting 2 testing doses below the maximum tolerated dose of each of temozolomide and carboxyamidotriazole orotate, according to method of claim 2
    (3) designing 4 combinatorial doses a) to d) by combing the 2 testing dose levels of temozolomide with the 2 testing dose levels of carboxyamidotriazole orotate and testing them in normal animals to determine the optimum dose for achieving therapeutic levels in blood with least toxicity according to claim 2, and
    (4) testing the optimum dose determined in (3) in tumored animals implanted with tumors, to determine the combinatorial dose with maximum antitumor activity and least toxicity, according to claim 3.

* * * * *